United States Patent [19]

Castelijns et al.

[11] Patent Number: 5,334,721

[45] Date of Patent: Aug. 2, 1994

[54] 2,4-DIMETHYL-5-OXOHEXANE AND A METHOD OF USE THEREFOR

[75] Inventors: Anna M. C. F. Castelijns, Stein; Henricus J. Arts, Sittard; Richard Green, Geleen, all of Netherlands

[73] Assignee: Stamicarbon B.V., Geleen, Netherlands

[21] Appl. No.: 98,909

[22] Filed: Jul. 29, 1993

Related U.S. Application Data

[60] Division of Ser. No. 902,785, Jun. 24, 1992, Pat. No. 5,254,712, which is a continuation of Ser. No. 638,397, Jan. 7, 1991, abandoned.

[30] Foreign Application Priority Data

Jan. 6, 1990 [NL] Netherlands .................. 9000034

[51] Int. Cl.$^5$ .................. C07D 213/09; C07D 213/12
[52] U.S. Cl. .................. 546/251; 558/368; 558/440
[58] Field of Search .................. 558/440, 368; 546/251

[56] References Cited

U.S. PATENT DOCUMENTS

| | | | |
|---|---|---|---|
| 2,381,371 | 8/1945 | Shannon | 558/368 |
| 2,579,580 | 12/1951 | Howk et al. | 260/465 J |
| 2,850,519 | 9/1958 | Krimm | 558/368 |
| 3,007,931 | 11/1961 | Simpson et al. | 546/251 X |
| 3,816,503 | 6/1974 | Von Poelvoorde et al. | 558/368 |
| 4,005,227 | 1/1977 | Winter et al. | 546/348 X |
| 4,117,000 | 9/1978 | Balg et al. | 558/368 |
| 4,245,098 | 1/1981 | Steiner et al. | 548/440 X |
| 4,267,362 | 5/1981 | Meyer et al. | 558/368 X |
| 4,276,419 | 6/1981 | Verheijen et al. | 546/251 X |
| 4,294,968 | 10/1981 | Stone et al. | 546/251 |
| 4,386,207 | 5/1983 | de Graaf et al. | 546/251 X |
| 4,405,552 | 9/1983 | Miesel | 546/309 X |
| 4,468,354 | 8/1984 | Lysenko et al. | 558/368 |
| 4,577,028 | 3/1986 | Martin et al. | 546/345 |
| 4,599,422 | 7/1986 | Amey | 546/251 |
| 4,665,186 | 5/1987 | Steiner et al. | 546/250 |
| 4,897,484 | 1/1990 | Weis et al. | 546/250 X |
| 4,996,323 | 2/1991 | Pews | 558/440 X |
| 5,053,516 | 10/1991 | Hartmann et al. | 546/251 |

FOREIGN PATENT DOCUMENTS

1304155 1/1973 United Kingdom .

OTHER PUBLICATIONS

Ono, et. al., C.A, 94:120797c (1981).
Ogigin, et. al., C.A., 94:173976s (1981).
Troyanskii, et. al., C.A., 96:103603k (1982).
Levinson, et. al., C.A., 97:92140z (1982).
Fuji, C.A., 99:21958c (1983).
Williams, et. al., C.A. 113:191050a (1990).
Organic Reactions, vol. 5, pp. 130–133, (1949) (in Chapter 2 on "Eyonoethylation"by Breeson).
Ono et. al., "A Novel Synthesis of (+)-Serricornin 4,6-Dimethyl-7-hydroxy-nonan-3-one" The Sex Pheromone of Cigarette Beetle (Lasioderma serricorne F.), Agric. Biol. Chem., 44(9), pp. 2259–2260, (1980).
March, "Advanced Organic Chemistry" Reactions, Mechanisms, and Structure, A Wiley–Interscience Publication by John Wiley & Sons, Third Edition, pp. 16–18, (1971).

*Primary Examiner*—Joseph Paul Brust

[57] ABSTRACT

The invention relates to a process for the preparation of high yields of 5-oxohexane nitriles with minimum formation of 1 undesired isomer. Such nitriles may be utilized as starting materials for the preparation of pharmaceutical and agrochemical intermediates and as well as final products. The process comprises reacting a methyl ketone and an $\alpha,\beta$-unsaturated nitrile in the presence of a catalytically effective amount of a strong base. One of the products which may be created by the process is 2,4-dimethyl-5-oxohexane nitrile.

14 Claims, No Drawings

2,4-DIMETHYL-5-OXOHEXANE AND A METHOD OF USE THEREFOR

RELATED APPLICATIONS

This application is a division of application 07/902,785 filed Jun. 24, 1992 now U.S. Pat. No. 5,254,172, which is a continuation of application 07/638,397 filed Jan. 7, 1991, now abandoned.

BACKGROUND OF THE INVENTION

1. Technical Field

The invention relates to a process for the preparation of high yields of 5-oxohexane nitriles. Such nitriles are formulated by catalytic conversion of a methyl ketone and an α,β-unsaturated nitrile in the presence of a strong base.

One type of 5-oxohexane nitrile which can be created using the present process is 2,4-dimethyl-5-oxohexane nitrile.

2. Background Information

A related process is known from US patent specification U.S. Pat. No. 2,850,519. In particular, this publication describes the reaction of acrylic acid nitrile and ketones in the presence of primary amines as catalysts. It has appeared, however, that when asymmetrical methyl ketones are used in this process, as starting material in combination with other nitriles than acrylic acid nitrile (e.g. methacrylic acid nitrile), isomer mixtures are formed that contain a substantial amount of undesired isomer, namely the product of addition of the α,β-unsaturated nitrile to the methyl group of the ketone, whereas this is not the case when acrylic acid nitrile is used as starting material in such a reaction. Furthermore, isolation of the isomers generally is very difficult.

As a consequence, the yield in which the 5-oxohexane nitriles can be obtained in purified form, that is, with less than 0.2 wt. % of undesired fisomer, generally is very low, as a major part of the nitrile is lost in the separation process.

SUMMARY OF THE INVENTION

According to the invention, a process is provided for the production of high yields of 5-oxohexane nitriles with minimum formation of 1 undesirable isomer which comprises reacting a methyl ketone and an α,β-unsaturated nitrile in the presence of a catalytically effective amount of a strong base.

Further, according to the invention, the ketone comprises a methyl ketone having an electron-donating group with 1-20 carbon atoms, the nitrile comprises an α,β-unsaturated nitrile having at least one substituent that is not hydrogen, and the strong base comprises an alkali metal hydroxide.

In one embodiment, the invention relates to a process for the preparation of 5-oxohexane nitriles according to Formula 1,

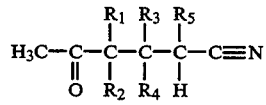

Formula 1 where at least $R_1$ or $R_2$ is not hydrogen. Such nitriles are formulated by catalytic conversion of a methyl ketone according to Formula 2

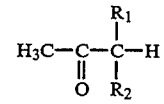

Formula 2 where $R_1$ and $R_2$ denote the same as in Formula 1, and an α,β-unsaturated nitrile according to Formula 3.

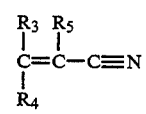

Formula 3

In Formula 2, $R_1$ or $R_2$ is an electron-donating group with 1-20 carbon atoms, such as an alkyl, alkenyl, cycloalkyl or alkoxy group. Furthermore, these groups may or may not be substituted. In Formula 3, one of the groups $R_3$, $R_4$ or $R_5$ is not hydrogen.

Another embodiment of the present invention relates to the novel compound 2,4-dimethyl-5-oxohexane nitrile.

All U.S. patents referred to herein are hereby incorporated by reference.

DETAILED DESCRIPTION OF THE INVENTION

The object of the process, according to the present invention, is to substantially avoid the formation of undesired isomers.

According to the invention, this is achieved when $R_1$ or $R_2$ is an electron-donating group with 1-20 carbon atoms and when at least one of the groups $R_3$, $R_4$ or $R_5$ is not hydrogen. Furthermore, a strong base must be utilized as a catalyst.

The use of a strong base in general as a catalyst for this type of reaction, in particular, in cyanoethylation reactions with acrylic acid nitrile, is known per se. However, it has been generally assumed, as for example is illustrated in U.S. Pat. No. 2,850,519, that the use of a strong base is disadvantageous since the yield of the desired product would be low due to side reactions such as, for instance, aldol condensation of ketones, and the formation of polycyanoethylated products when the ketones have two or more active hydrogen atoms.

The invention also relates to the new compound 2,4-dimethyl-5-oxohexane nitrile. U.S. Pat. No. 4,647,686 discloses a general method for the preparation of 5-oxohexane nitriles from corresponding cycloalkanones. However, the patent does not disclose the particular cyclopentanone used as starting material for the formation of the 2,4-dimethyl-5-oxohexane nitrile of the present method, i.e., 2,3,5-trimethyl cyclopentanone.

The need for a method for the preparation of 5-oxohexane nitriles according to Formula 1, in which at least $R_1$ or $R_2$ and at least one of the groups $R_3$, $R_4$, or $R_5$ is not hydrogen, results from the demand for pure 5-oxohexane nitriles among the users of these compounds or of compounds that can be prepared from them. 5-Oxohexane nitriles are used as starting materials for pharmaceutical and agrochemical intermediates and final products.

A specific application of the 5-oxohexane nitriles according to Formula 1, where $R_2$ and $R_4$ are hydrogen and at least $R_1$ and at least $R_3$ or $R_5$ is not hydrogen, is the preparation of 2-methyl pyridines according to Formula 4:

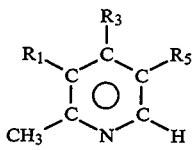

Formula 4

A number of these pyridine derivatives are important starting materials for the preparation of pharmaceutical products. In the preparation of such products, often strict demands with respect to the purity of the starting materials must be met. A requirement of less than 0.2 wt. % of undesirable pyridine derivatives is not uncommon.

In many cases, it is impossible to effect adequate separation of a mixture of isomeric pyridine derivatives at acceptable costs, particularly when large amounts of undesirable pyridine isomers need to be isolated.

A method for the preparation of the above-mentioned 2-methyl pyridines having a high purity, so that the separation problem is obviated, is the catalytic cyclization and dehydrogenation of 5-oxohexane nitriles according to Formula 1, where $R_2$ and $R_4$ are hydrogen and at least $R_1$ and at least $R_3$ or $R_5$ is not hydrogen, according to a process known per se. The cyclization and dehydrogenation occur, for instance, in the gas phase. A condition to be satisfied for high purity of the final product is that the nitrile must also have a very low content of undesirable isomer.

The process according to the invention can be used to prepare nitriles having a low content of undesirable isomers.

One of the substances that can be prepared using the process according to the invention is the novel substance 2,4-dimethyl- 5-oxohexane nitrile. From this substance, 2,3,5-trimethyl pyridine can be prepared by means of, for instance, catalytic gas-phase cyclization and dehydrogenation as described in UK patent specification GB-A-1304155.

2,3,5-Trimethyl pyridine, among other things, is a starting material for pharmaceutical preparations which regulate the secretion of gastric acid. For this application, the above-mentioned considerations relating to the purity of the products certainly hold.

Most of the preparation methods for 2,3,5-trimethyl pyridine currently known start from substituted pyridine derivatives. According to, for instance, US patent specification U.S. Pat. No. 4,658,032, 2,3,5-trimethyl pyridine can be prepared from 3,5-lutidine by reacting this substance with an alcohol in the presence of an hydrogenation catalyst at a temperature of 200° C. or higher. A drawback of this method is the very high catalyst consumption. Another drawback of this preparation method, and in general of preparation methods starting from pyridines, substituted or not, is that the pyridines used as starting material themselves often are hard to obtain.

These drawbacks do not present themselves in the preparation of 2,3,5-trimethyl pyridine starting from 2,4-dimethyl-5-oxohexane nitrile.

The major problem in the present preparation method was how to obtain the starting material, 2,4-dimethyl-5-oxohexane nitrile, in sufficiently pure form. The thusfar known preparation methods which offer the highest yields of 2,4-dimethyl-5-oxohexane, in cyanoethylation reactions of ketones with acrylic acid nitrile, such as those described in the above-mentioned U.S. patent specification U.S. Pat. No. 2,850,519, have as byproduct substantial amounts (desirable isomer:undesirable isomer=about 2:1) of 2-methyl-5-oxoheptane nitrile:

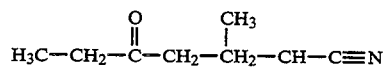

Separation of 2-methyl-5-oxoheptane nitrile and 2,4-dimethyl-5-oxohexane nitrile is very difficult, but it is necessary because gas phase cyclization of 2-methyl-5-oxoheptane nitrile yields 2-ethyl-5-methyl pyridine as product, which is undesirable and which, in addition, is difficult to isolate from 2,3,5-trimethyl pyridine.

With the process according to the invention, the formation of 2-methyl-5-oxoheptane nitrile during the preparation of 2,4-dimethyl-5-oxohexane nitrile can to a large extent be prevented. An isomer ratio of about 10:1 can be achieved, as opposed to about 2:1 with the known processes.

The ketones to be used in the process according to the invention are ketones according to Formula 2 wherein $R_1$ or $R_2$ is an electron-donating group with 1–20 carbon atoms. Examples of such groups are: alkyl or alkenyl, substituted or not, cycloalkyl, substituted or not, and alkoxy, substituted or not. Suitable substituents are substituents that are stable under reaction conditions, such as, for instance, alkoxy, aryl and heteroaryl groups with 1–10 carbon atoms. Examples of suitable ketones are: butanone, pentane-2-one, hexane-2-one, methoxy-acetone, heptane-2-one, and 3-methyl-pentane-2-one, 4-methyl-pentane-2-one, and benzyloxyacetone.

The nitriles that can be used in the process are nitriles according to Formula 3 where at least one of the groups $R_3$, $R_4$ or $R_5$ is not hydrogen. Suitable choices for $R_3$, $R_4$, or $R_5$ are electron-donating groups with 1–20 carbon atoms. Examples of such groups are: alkyl or alkenyl, substituted or not, cycloalkyl, substituted or not, alkoxy, substituted or not. Suitable substituents are those that are stable under reaction conditions, such as, for instance, alkoxy, aryl and heteroaryl. Most of the electron-donating groups will contain fewer than 7 carbon atoms. Examples of nitriles are methacrylic acid nitrile, 2-cyano-1-butene, 2-cyano-1-pentene, 2-cyano-1-hexene, 2-cyano-2-butene, crotonic nitrile, 3-cyclohexyl-2-cyano-1-butene, and 2-cyclohexyl propene nitrile.

A suitable way of carrying out the process is as follows:

The ketone, the nitrile, the strong base and optionally an inert solvent are combined. The sequence in which the components are added as well as the feed rates are not particularly critical. The components may be combined before the reaction, but it is also possible to add one or more components entirely or partly during the reaction. The reaction mixture is heated to the reaction temperature and kept at this temperature for some time. Upon completion of the reaction, the reaction mixture is, if necessary, cooled to room temperature. The reaction mixture is subsequently neutralized and the organic phase is washed. Non-converted reactants and any solvent present are removed, for instance by evaporation, optionally at reduced pressure, and the product is recovered by distillation, also optionally at reduced pressure.

The molar ratio of ketone/nitrile in general is not critical and can be varied within broad limits. The highest yields are generally obtained when an excess of ketone is used. The ratio of ketone to nitrile is preferably between 2:1 and 7:1, and more preferably between 3:1 and 5:1.

As catalyst, in principle, any strong base can be used such as, for instance, an alkali metal. Examples of suitable catalysts include alkali alkanolates, alkali hydroxides, tetra-alkyl ammonium hydroxides (e.g. Triton B), alkali hydrides, and alkali amides. Very good results are achieved when use is made of tetra-alkyl ammonium hydroxides.

The base can be added in many ways. Depending on its physical characteristics, the base may for instance be added as a solution in water, a solution in an alcohol such as methanol, or in solid form.

The concentration of the base in the organic phase can be varied within broad limits. By varying the concentration, the reaction velocity can be influenced; a higher concentration yields a higher velocity.

By preference, use is made of sodium hydroxide or potassium hydroxide. If the alkali hydroxide is added as an aqueous solution, this is preferably done in a concentration of more than 10 wt. %, and more preferably in a concentration of more than 40 wt. %.

The use of a base as a solid, for instance sodium hydroxide in powder form, generally results in high reaction velocities. Another very suitable form of base application is as a solution in methanol, preferably a saturated solution in methanol. The use of alkali hydroxide as a base yields the best results.

The temperature during the reaction is not particularly critical. A suitable temperature is the reflux temperature of the reaction mixture. This may vary within broad limits, depending on the mixture. However, in a number of cases, it is quite possible to carry out the reaction at room temperature. It also is possible to use higher temperatures when working under elevated pressure in an autoclave. Temperatures below the reflux temperature generally decrease the reaction velocity.

Several methods are suitable for upgrading of the mixture. One of these is the neutralization of the crude reaction mixture. After this, the reaction mixture can be washed by treating it several times with a salt solution. After these washing treatments, the non-converted starting materials and any solvent present can be removed by evaporation, optionally under reduced pressure. The product can then be recovered by distillation.

The process according to the invention will now be elucidated with reference to the following examples, without being restricted thereto.

In the description of the examples and in the tables, the following symbols have the meanings denoted below:

MACN: methacrylic acid nitrile
ACN: acrylic acid nitrile
BzOH: benzoic acid
A: 2,4-dimethyl-5-oxohexane nitrile
B: 2-methyl-5-oxoheptane nitrile
C: 4-methyl-5-oxohexane nitrile
D: 5-oxoheptane nitrile
conv.: conversion
sel.: selectivity
t: reaction time
T: temperature
m.r.: molar ratio

EXAMPLE I

Ia. Preparation of A 288.0 g of butanone (4.0 mol) and 67 g of MACN (1.0 mol) were introduced into a 500 ml round bottom flask, equipped with a thermometer, cooler and stirrer. With stirring, 8.75 g of a 15 wt. % NaOH solution in methanol (0.033 mol NaOH) was added. The reaction mixture was heated up to reflux (heating time approx. 14 minutes, reflux temperature 81° C.). After a total reaction time of 90 minutes, the mixture was cooled to room temperature. Gas chromatographic analysis showed that about 99.0% of the MACN supplied had been converted, and about 5.7% of the butanone supplied. Calculated relative to converted NACN, the yield in terms of A was 36.4% and in terms of B, 3.4%. Calculated relative to converted butanone these yields are approximately 0.5% and 2.9%, respectively. (Ratio of A:B=0.6:1). The results are presented in Table 1.

Ib. Purification

The reaction mixture was subsequently neutralized using 16.1 g of 10% $H_2SO_4$ solution in $H_2O$. Fifty ml of a 10 wt. % solution of $Na_2SO_4$ in water was then added. After demixing of the two phases, the water phase was separated off, and the organic phase was washed with 50 ml of a 10 wt. % $Na_2SO_4$ solutions. The excess butanone was evaporated from the organic phase using the rotavapor, the residue being subjected to vacuum distillation using a packed column with approx. 40 practical trays. At a pressure of 15 mm Hg, the main fraction came off at the top with a temperature of 110°–113° C. In this manner, 40.75 g of distillate was obtained. Gas chromatographic analysis showed this distillate to contain 40.1 g of A and 0.04 g of B (ratio of A:B=1000:1).

EXAMPLES II TO IX

An amount of a strong base was added to a mixture of butanone and MACN. The base was optionally in the form of solution. The reaction mixture was then brought to a certain temperature and maintained there during a number of hours. The mixture was subsequently analyzed gas chromatographically. The procedure followed was analogous to that of Example Ia. The results are presented in Table 1.

TABLE 1

| base | m.r. butanone MACN | m.r. MACN base | T °C. | t hr | conv. butanone (%) | conv. MACN (%) | butanone sel. towards A | butanone sel. towards B | MACN sel. towards A | MACN sel. towards B | A/B |
|---|---|---|---|---|---|---|---|---|---|---|---|
| Ia 15% NaOH in $CH_3OH$ | 4 | 30 | 80–85 | 1.5 | 25.7 | 99 | 30.5 | 2.9 | 36.4 | 3.4 | 10.6 |
| II KOtBu in tBuOH (5.7 wt. % sol.) | 5 | 10 | 25–30 | 3 | 17.4 | 100 | 30.4 | 2.2 | 26.2 | 1.9 | 13.8 |
| III 50% NaOH in $H_2O$ | 3 | 10 | 75–80 | 6 | 28.8 | 99.8 | 28.1 | 2.9 | 24.4 | 2.5 | 9.6 |
| IV 10% NaOH in $H_2O$ | 3 | 2.5 | 75–80 | 6 | 9.3 | 42.4 | 13.4 | 1.3 | 8.8 | 0.9 | 10 |
| V solid NaOH (powder) | 3 | 45 | 75–80 | 3 | 26.7 | 99.7 | 33.3 | 3.3 | 26.7 | 2.7 | 10 |
| VI Triton B | 5 | 10 | 28–32 | 3 | 14.5 | 100 | 34.3 | 1.3 | 24.9 | 0.9 | 27.7 |
| VII 20% KOH in $CH_3OH$ | 3 | 45 | 75–80 | 1.75 | 23.2 | 97.7 | 37.5 | 3.5 | 26.2 | 2.4 | 10.7 |

TABLE 1-continued

| base | m.r. butanone MACN | m.r. MACN base | T °C. | t hr | conv. butanone (%) | conv. MACN (%) | butanone sel. towards A | butanone sel. towards B | MACN sel. towards A | MACN sel. towards B | A/B |
|---|---|---|---|---|---|---|---|---|---|---|---|
| VIII 15% NaOH in CH3OH | 3 | 30 | 75–80 | 1 | 29.5 | 96.5 | 29.4 | 2.8 | 26.9 | 2.6 | 10.4 |
| IX 15% NaOH in CH3OH | 5 | 30 | 75–80 | 1 | 21.9 | 91.1 | 31.1 | 2.9 | 37.4 | 3.5 | 10.7 |

COMPARATIVE EXPERIMENT 10

10.a. Preparation of A

A 2 l. autoclave was charged with 538 g of butanone, 167 g of MACN, 94 g of n-propyl amine and 0.6 g of BzOH. The mixture was subsequently heated at 180° C. under autogenous pressure for 6 hours while being stirred. The pressure initially was 11 bar, decreasing to 9 bar at the end of the reaction. The reaction mixture was subsequently cooled.

According to gas chromatographic analysis, about 83.3% of the MACN used had been converted and about 28.1% of the butanone used. Calculated relative to converted MACN, the yield in terms of A was 36.4% and in terms of B, 18.3%. Calculated relative to converted butanone, these yields are about 36.1% and 18.1%, respectively (ratio of A:B=2:1). The results are presented in Table 2.

10.b. Purification

Using the rotavapor, subsequently the larger part of the non-converted butanone, MACN and n-propyl amine were evaporated. After evaporation of the volatile components, 361 g of reaction mixture remained. To this mixture, an equal volume (about 400 ml) of water containing about 4 wt. % HCl was added, followed by heating for 1 hour at 95° C. with stirring.

Subsequently, the organic phase was separated off, and the aqueous phase was extracted 4× with about 20 ml of CH2Cl2. The CH2Cl2 extracts were added to the organic phase. After drying of the organic phase over MgSO4 and rotavapor evaporation at room temperature, 348.5 g of residue remained, which was distilled using a sieve tray column (approx. 30 practical trays) at reduced pressure. At a pressure of 12 mm Hg, the main fraction came off at the top at a temperature of 100°–107° C. In this manner, 143.2 g of distillate was obtained. According to gas chromatographic analysis, this distillate contained 108 g of A and 29.5 g of B (ratio of A:B=3.7:1).

COMPARATIVE EXPERIMENTS 11 to 15

In a 50 ml autoclave, a mixture of butanone, MACN, amine and BzOH was heated for 6 hours at a certain temperature. After cooling, the reaction mixture was analyzed gas chromatographically. The procedure was analogous to that of Comparative experiment 10a.

The results of these experiments are presented in Table 2. These examples show that using primary amines as a catalyst in the reaction of ketones with methacrylic acid nitrile, a relatively large amount of the undesired isomer (B) is formed.

COMPARATIVE EXPERIMENT 16

2 l. A autoclave was charged with 538 g of butanone, 132.5 g ACN, 6.36 g ethylenediamine and 0.82 g BzOH. The mixture was subsequently heated at 140° C. under autogenous pressure for 6 hours while being stirred. The reaction mixture was subsequently cooled.

According to gas chromatographic analysis, about 91.8% of the ACN used had been converted and about 29.6% of the butanone used. Calculated relative to converted ACN, the yield in terms of C was 69.9% and in terms of D, 6.8%. Calculated relative to converted butanone, these yields are about 71.7% and 7.1%, respectively (ratio C:D=10:1). This experiment shows that when acrylic acid nitrile is used, instead of methacrylic acid nitrile, the use of primary amines as a catalyst does not result in the formation of large amounts of the undesired isomer.

TABLE 2

| amine | m.r. butanone MACN | m.r. MACN amine | m.r. amine B % OH | T °C. | conv. butanone (%) | conv. MACN (%) | butanone sel. towards A | butanone sel. towards B | MACN sel. towards A | MACN sel. towards B | A/B |
|---|---|---|---|---|---|---|---|---|---|---|---|
| 10a. n-propylamine | 3 | 1.6 | 320 | 180 | 28.1 | 83.3 | 36.1 | 18.1 | 36.4 | 18.3 | 2.0 |
| 11. isopropylamine | 3 | 6.7 | 83.7 | 180 | nihil | nihil | — | — | — | — | — |
| 12. ethyleendiamine | 3 | 3.1 | 160 | 180 | 37.3 | 79.9 | 22.1 | 7.5 | 31.0 | 10.5 | 2.9 |
| 13. n-propylamine | 4 | 1.6 | 242 | 180 | 29.4 | 81.2 | 38.4 | 11.9 | 40.9 | 12.7 | 3.2 |
| 14. n-propylamine | 3 | 1.9 | 262 | 200 | 53.0 | 93.5 | 18.1 | 10.7 | 30.6 | 18.1 | 1.7 |
| 15. n-propylamine | 3 | 1.9 | 262 | 220 | 56.7 | 99.1 | 9.6 | 7.9 | 16.4 | 13.4 | 1.2 |

What is claimed is:

1. A process for the preparation of a 2-methyl-3,5-dialkylpyridine represented by the formula:

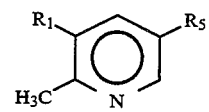

wherein $R_1$ and $R_5$ are independently of one another a $C_1$ to $C_{20}$ alkyl group comprising:

allowing a methyl ketone represented by the formula:

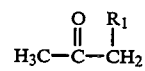

wherein $R_1$ is as defined above, and an $\alpha,\beta$-unsaturated nitrile represented by the formula:

$$\begin{array}{c} R_3\ R_5 \\ |\ \ | \\ HC{=}C{-}C{\equiv}N \end{array}$$

wherein $R_3$ is H and $R_5$ is as defined above, to react in the presence of a catalytically effective amount of a strong base which is sufficient to promote the formation a 2,4-dialkyl-5-oxohexane nitrile represented by the formula:

$$\begin{array}{c} O\ \ \ \ R_1\ \ \ \ \ \ \ \ \ \ R_5 \\ \|\ \ \ \ |\ \ \ \ \ \ \ \ \ \ \ | \\ H_3C{-}C{-}CH{-}CH_2{-}CH{-}C{\equiv}N \end{array}$$

wherein $R_1$ and $R_5$ are as defined above, in high yield and in the substantial absence of undesired isomers; and catalytically cyclizing and dehydrogenating the 2,4-dialkyl-5-oxohexane nitrile whereby the 2-methyl-3,5-dialkyl pyridine is obtained.

2. A process for the preparation of a 2-methyl-3,5-dialkylpyridine according to claim 1, wherein the pyridine is 2,3,5-trimethyl pyridine, and wherein said 2,4-dialkyl-5-oxohexane nitrile is 2,4-dimethyl-5-oxohexane nitrile.

3. A process according to claim 1, wherein said $\alpha,\beta$-unsaturated nitrile is allowed to react with an excess of said methyl ketone in the presence of a catalytically effective amount of a strong base to promote the preparation of the desired 5-oxohexane-nitrile at a ratio of about 10:1 and greater to the production of undesired isomers resulting from the reaction of the methyl group of said methyl ketone with said $\alpha,\beta$-unsaturated nitrile.

4. A process according to claim 3, wherein said strong base is an alkali metal hydroxide.

5. A process according to claim 4, wherein said alkali metal hydroxide is sodium hydroxide or potassium hydroxide.

6. A process according to claim 3, wherein said strong base is a solution in an alcohol.

7. A process according to claim 3, wherein said strong base is an aqueous solution in the concentration of the strong base in the aqueous solution is greater than 10 weight percent.

8. A process according to claim 3, wherein said strong base is a tetra-alkyl ammonium hydroxide.

9. A process according to claim 3, wherein the ketone is provided in excess compared to the nitrile.

10. A process according to claim 8, wherein the ketone and nitrile are present at a molar ratio of between 2:1 and 7:1.

11. A process according to claim 10, wherein said molar ratio is between 3:1 and 5:1.

12. A process according to claim 3, wherein said $\alpha,\beta$-unsaturated nitrile is methacrylic acid nitrile wherein $R_5$ is methyl and $R_3$ and $R_4$ are hydrogen.

13. A process according to claim 3, wherein said $\alpha,\beta$-unsaturated nitrile is methacrylic acid nitrile, said asymmetrical methyl ketone is butanone, said strong base is an alkali metal hydroxide, the desired isomer is 2,4-dimethyl-5-oxohexane nitrile, and the undesired isomer is 2-methyl-5-oxohexane nitrile.

14. A process for the preparation of a 2-methylpyridine compound represented by the formula (A):

[pyridine ring structure with $R_1$, $R_3$, $R_5$ substituents and $H_3C$ at 2-position]

wherein $R_1$ is a $C_1$ to $C_{20}$ alkyl group, $R_3$ and $R_5$ are both independently H or a $C_1$ to $C_{20}$ alkyl group but $R_3$ and $R_5$ are not both H, comprising allowing a methylketone represented by the formula $$\begin{array}{c} O\ \ \ \ R_1 \\ \|\ \ \ \ | \\ H_3C{-}C{-}CH_2 \end{array}$$

wherein $R_1$ is as defined above, to react with an $\alpha,\beta$-unsaturated nitrile represented by the formula:

$$\begin{array}{c} R_3\ R_5 \\ |\ \ | \\ HC{=}C{-}C{\equiv}N \end{array}$$

wherein $R_3$ and $R_5$ are as defined above in the presence of a catalytically effective amount of a strong base which is sufficient to promote the formation of a 5-oxohexane nitrile represented by the formula $$\begin{array}{c} O\ \ \ \ R_1\ \ \ \ R_3\ \ \ \ R_5 \\ \|\ \ \ \ |\ \ \ \ \ |\ \ \ \ \ | \\ H_3C{-}C{-}CH{-}CH{-}CH{-}C{\equiv}N \end{array}$$

wherein $R_1$, $R_3$ and $R_5$ are as defined above, in high yields and in the substantial absence of undesired isomers, and catalytically cyclizing and dehydrogenating the 5-oxohexane nitrile whereby a 2-methylpyridine compound represented by formula (A) is obtained.

* * * * *